United States Patent [19]
Dohi et al.

[11] Patent Number: 5,880,322
[45] Date of Patent: Mar. 9, 1999

[54] METHOD FOR PRODUCING DIARYLMETHANE

[75] Inventors: Hideyuki Dohi; Syozo Hayashi, both of Yokohama, Japan

[73] Assignee: Nippen Petrochemicals Company, Limited, Tokyo, Japan

[21] Appl. No.: 988,829

[22] Filed: Dec. 11, 1997

[30] Foreign Application Priority Data

Dec. 16, 1996 [JP] Japan .................................. 8-353245

[51] Int. Cl.$^6$ .................................. C07C 1/20; C07C 2/66
[52] U.S. Cl. ........................ 585/469; 585/446; 585/467
[58] Field of Search ...................... 585/446, 467, 585/469

[56] References Cited

U.S. PATENT DOCUMENTS

| | | | |
|---|---|---|---|
| Re. 29,857 | 12/1978 | Argauer et al. | 208/111 |
| Re. 32,162 | 5/1986 | Sato et al. | 346/213 |
| 1,908,190 | 5/1933 | Scholkopf | 585/469 |
| 2,282,327 | 5/1942 | Dreisbach | 260/668 |
| 3,702,886 | 11/1972 | Argauer et al. | 423/328 |
| 3,758,403 | 9/1973 | Rosinski et al. | 208/120 |
| 3,786,107 | 1/1974 | Kuribayashi et al. | 260/672 T |
| 3,790,471 | 2/1974 | Argauer et al. | 208/111 |
| 3,836,383 | 9/1974 | Kritani et al. | 117/36.2 |
| 3,926,782 | 12/1975 | Plank et al. | 208/135 |
| 3,936,566 | 2/1976 | Sato et al. | 428/323 |
| 3,965,209 | 6/1976 | Butter et al. | 260/671 |
| 4,011,274 | 3/1977 | Wanatabe et al. | 260/668 |
| 4,035,285 | 7/1977 | Owen et al. | 208/120 |
| 4,111,825 | 9/1978 | Schulz et al. | 252/63 |
| 4,117,026 | 9/1978 | Haag et al. | 206/671 R |
| 4,219,687 | 8/1980 | Dolhyji et al. | 585/267 |
| 4,228,024 | 10/1980 | Schulz et al. | 252/63 |
| 4,289,806 | 9/1981 | Sato et al. | 427/150 |
| 4,365,103 | 12/1982 | Chang et al. | 585/320 |
| 4,454,364 | 6/1984 | Farcasui et al. | 585/470 |
| 4,463,209 | 7/1984 | Kursewicz et al. | 585/467 |
| 4,523,044 | 6/1985 | Commandeur et al. | 585/11 |
| 4,642,730 | 2/1987 | Sato et al. | 361/315 |
| 4,681,980 | 7/1987 | Sato et al. | 585/6.3 |
| 4,686,548 | 8/1987 | Takahashi et al. | 503/213 |
| 4,870,221 | 9/1989 | Sato et al. | 585/6.3 |
| 4,895,988 | 1/1990 | Clerici et al. | 568/727 |
| 4,899,009 | 2/1990 | Kawakami et al. | 585/471 |
| 4,902,841 | 2/1990 | Kawakami et al. | 585/6.3 |
| 4,982,025 | 1/1991 | Kawakami et al. | 585/6.3 |
| 5,068,481 | 11/1991 | Akatsu et al. | 585/426 |
| 5,073,655 | 12/1991 | Angevine et al. | 585/467 |
| 5,171,906 | 12/1992 | Kawakami et al. | 585/25 |

FOREIGN PATENT DOCUMENTS

| | | |
|---|---|---|
| 3127905 | 2/1983 | Germany . |
| 46-10064 | 3/1971 | Japan . |
| 1-180835 | 7/1989 | Japan . |

OTHER PUBLICATIONS

J. Chem. Soc. Jap., Ind. Chem. Sect. 72[7](1969) pp. 1512–15 (with english abstract attached).

*Primary Examiner*—Walter D. Griffen
*Assistant Examiner*—Tam M. Nguyen
*Attorney, Agent, or Firm*—Fisher, Christen & Sabol

[57] ABSTRACT

A method for producing diarylalkanes at a high yield using an aromatic hydrocarbon and inexpensive formalin in the presence of an easily usable solid acid catalyst, and in the method, a mixture of an aromatic hydrocarbon and formalin, said mixture containing 1.5 to 12% by weight of water, is reacted at a temperature of 170 to 450° C. under an elevated pressure in the presence of a zeolitic catalyst.

6 Claims, No Drawings

METHOD FOR PRODUCING DIARYLMETHANE

BACKGROUND OF THE INVENTION (1) Field of the Invention

This invention relates to an improved method for producing diarylmethanes. More particularly, the invention relates to a method for producing diarylmethanes using formalin, which diarylmethanes are useful as high boiling aromatic solvents and for various kinds of chemical products.

(2) Prior Art

Several methods have been proposed for producing diphenylmethane by condensing benzene with formaldehyde and for preparing dihydroxy diphenylmethane by condensing phenol and formaldehyde.

However, the handling of formaldehyde is difficult because it is a gaseous substance at ordinary temperatures. So that, as the material to be fed to a reaction system, paraformaldehyde and trioxane are practically used, which are in solid state at ordinary temperatures.

Meanwhile, the formaldehyde is usually supplied by makers in the form of an aqueous solution of formaldehyde, the so-called formalin. Therefore, in industrial production, the above-mentioned paraformaldehyde and trioxane are often prepared from the above aqueous solution that are supplied by makers. Accordingly, if it is possible to use the formaldehyde in the form of an aqueous solution for the reaction with the foregoing aromatic hydrocarbon, it is quite advantageous to reduce the cost for formaldehyde in industrial practice because it is possible to use the inexpensive material supplied by makers of formaldehyde.

However, this has been scarcely tried in the conventional art. One of the reasons is that, if an aqueous solution is supplied as a reaction material, the catalyst such as sulfuric acid and aluminum chloride that are useful for the condensation of formaldehyde, cannot be employed because they are water-soluble.

As a countermeasure to this problem, the reaction between phenol and formalin in the presence of solid acid catalysts such as zeolites is disclosed in Japanese Laid-Open Patent Publication No. 1-180835 and U.S. Pat. No. 4,895,988. These known methods are serviceable for the reaction of the aqueous solution of formaldehyde and phenols which are high in condensation activity with the formaldehyde. However, in the case of aromatic hydrocarbons such as benzene and toluene having low condensation activity, these methods are not always preferable in view of their low yields. Furthermore, any practicable method to condense benzene, toluene or xylene using formalin, has not been known.

BRIEF SUMMARY OF THE INVENTION

It is, therefore, a principal object of the present invention to provide a method for producing diarylmethanes using an inexpensive material of formalin as formaldehyde through the condensation of aromatic hydrocarbons and formaldehyde.

Another object of the present invention is to provide the method for producing diarylmethanes at a high yield using a solid acid catalyst that is used in industrial production without difficult.

Pursuant to the above objects, a first aspect of the present invention relates to a method for producing diarylmethanes which is characterized in that a mixture of an aromatic hydrocarbon and formalin containing 1.5 to 12% by weight of water, is reacted at a temperature of 170 to 450° C. under an elevated pressure in the presence of a zeolitic catalyst.

A second aspect of the present invention relates to a method for producing diarylmethanes, in which the aromatic hydrocarbon in the above first aspect is benzene, toluene or their mixture.

A third aspect of the present invention relates to a method for producing diarylmethanes, in which the zeolitic catalyst in the above first aspect is mordenite or pentasil type zeolite.

A fourth aspect of the present invention relates to a method for producing diarylmethanes, in which the reaction in any of the above first to third aspects, is carried out under an elevated pressure that is higher than the autogenous pressure.

In the method of the present invention, aromatic hydrocarbons and formalin are used as starting materials and it is possible to attain a high yield by employing the mixture of materials of low water content and by carrying out the reaction at a sufficiently high pressure. By the way, it is not desirable to apply the method of this invention to phenol because the yield of aimed product is low.

DETAILED DESCRIPTION OF THE INVENTION

In the following, the present invention will be described in more detail.

The aromatic hydrocarbons used in the present invention those having at least one hydrogen atom directly connected to a benzene ring such as benzene, naphthalene, and alkylbenzenes of toluene, xylene, ethylbenzene, cumene, trimethylbenzene, ethyltoluene, and diethylbenzene.

As will be understood in view of the above exemplar compounds, the benzene ring can have lower alkyl substituent group such as methyl, ethyl, propyl or butyl group besides hydrogen atoms. The alkyl substituent group can be plural. Furthermore, the plurality of alkyl groups may be the same ones or different.

When benzene and formalin are caused to react, diphenylmethane is produced. Likewise, when one kind of aromatic hydrocarbon is used, a symmetrical diarylmethane is produced. In order to prepare asymmetrical diarylmethane such as tolylphenylmethane, a mixture of two or more kinds of aromatic hydrocarbons, e.g., a mixture of benzene and toluene, is used.

The formalin used in the method of the present invention is an aqueous solution of formaldehyde which can contain methanol as a stabilizing agent. The formalin is generally supplied as an aqueous solution of formaldehyde of about 40% in concentration. The concentration is not restricted to such a value but it is possible to use the formalin of lower concentration. However, it is preferable that the concentration of formaldehyde (including dimer and higher polymers) in formalin is more than 20% by weight. Although the upper value of formaldehyde concentration is not limited as far as the formalin is in the state of an aqueous solution, the concentration is generally lower than 80% by weight. The formaldehyde exists generally in a hydrated form in the aqueous solution.

The molar ratio of the aromatic hydrocarbon to the formalin (aromatic hydrocarbon)/(formaldehyde) is in the range of 1 to 100, preferably 5 to 40.

When an aromatic hydrocarbon and formalin are fed to a reaction system, the quantities of them must be so adjusted that the content of water is in the range of 1.5 to 12% by weight.

For example, in a batchwise reaction, the formalin of required formaldehyde concentration is used, at the same time, the quantity of formalin is so adjusted that the quantity of water relative to the sum of aromatic hydrocarbon and formalin is in the above range. In this step, the molar ratio of the aromatic hydrocarbon and formaldehyde must be adjusted to the above-mentioned range. Of course, in a continuous flow system, the ratio of reactants in the reaction mixture must be adjusted also in the range as described above.

If the quantity of water exceeds 12% by weight, it is not desirable because the rate of reaction is too low. On the other hand, if the quantity of water is less than 1.5% by weight, the concentration of diarylmethane is low, which is not economical.

Therefore, for example, when an easily available 37 wt. % formalin containing 8 wt. % of methanol and toluene as an aromatic hydrocarbon are used, the use quantity of formalin is in the range of about 2.8 to 27.9 parts by weight to 100 parts by weight of toluene.

Various kinds of zeolites can be used in the method of the present invention. For example, in view of the types of crystalline structures, there are A type zeolite, X type zeolite, Y type zeolite, ultra-stabilized Y type zeolites, ZSM type zeolite and mordenite type zeolite. Among them, preferably used zeolites are those having pore-openings of 10-membered oxygen rings, those having pore-openings of 12-membered oxygen rings or their mixtures.

As the mordenite type zeolite, those of 5 or more in the molar ratio of silica/alumina, are used.

The pentasil type zeolite has a basic structure of 5-membered ring (pentasil skeletal structure), which is typically exemplified by ZSM-5 and silicalite. Those having the molar ratio of silica/alumina of 6 or more, preferably more than 20, are used. The methods for preparing ZSM-5 are disclosed, for example, in U.S. Pat. No. 3,702,886 and Japanese Patent Publication No. 46-10064.

Besides the above zeolites, there are known ZSM-11, ZSM-8, ZSM-5/ZSM-11 intermediate product, Zeta-1, Zeta-2, ZMB-10, Ultrazel, TZ-01, NU-4, NU-5, AZ-1, and mixtures of them.

When these zeolites are synthesized or obtained from a maker, they may be subjected to ion exchange treatment to replace $Na^+$ with proton, $Li^+$ or polyvalent positive ions. It is desirable that 50 to 100%, especially 80 to 100%, of exchangeable metallic cation is replaced with hydrogen ions.

Furthermore, the zeolite which is subjected to de-aluminum process with hydrothermal treatment or hydrochloric acid treatment, can also be employed.

In the following, as a method for synthesizing zeolite for use in the method of the present invention, the preparation of ZSM-5 is exemplified. A reactant mixture of tetrapropyl ammonium hydroxide, sodium oxide, aluminum oxide, silicon oxide and water is prepared according to the formulation described in the above patent gazettes. After that, hydrothermal synthesis is carried out by heating this reactant mixture. After the synthesis, the obtained crystals are baked in the air to obtain a ZSM-5 catalyst.

Meanwhile, the amorphous silica alumina is not suitable. as a catalyst for use in the method of the present invention because it is low in the activity to formalin and the selectivity to diarylalkane is also low.

The reaction temperature is arbitrarily selected from the range of 170 to 450° C., preferably above 200 to 450° C. The reaction temperature below 170° C. is not preferable because the rate of reaction is low and a byproduct such as benzyl alcohol is formed in the use of some catalysts. On the other hand, if the reaction temperature is higher than 450° C., it is not preferable because side reaction such as the transferring of alkyl groups is caused to occur. The pressure of reaction is not especially limited as far as the reaction is done under an elevated pressure and it is preferable that the reaction is carried out under a pressure above an autogenous pressure. More desirably, in the case that a reaction temperature is lower than the critical temperature of the reaction system, the reaction is done under a pressure which is higher than the vapor pressure generated by the reaction mixture at the reaction temperature. If the reaction temperature is higher than the critical temperature of the reaction system, the reaction is done near the critical pressure of the reaction system. More desirable pressure is selected, for example, from a value of 800 kPa or above.

The upper value of pressure is not limited as far as the pressure is higher than the above value. The upper limit of pressure is generally determined by the limit of the pressure resistance of apparatus and the cost for pressurizing operation, which value is usually lower than about 10 MPa.

The reaction according to the method of the present invention is carried out in any of a batchwise system and a continuous system. When the reaction is carried out in a continuous system, the liquid hourly space velocity (LHSV) is not limited. It is generally selected from the range of 0.1 to 300 $hr^{-1}$. As a reaction vessel, any of a fluidized bed reactor and a fixed bed reactor can be employed. The apparatus composed of a plurality of fixed bed reactors installed side-by-side can also be used.

In the case of batchwise system, the time length of reaction is different with the quantity of catalyst and the reaction temperature, however, it is in the range of 0.1 to 20 hours. The quantity of catalyst is 0.01 to 10 times, preferably 0.05 to 5 times by weight as much as the quantity of formaldehyde.

After the reaction, it is possible to recover the diarylmethane through a known separating method such as distillation.

In the following, the present invention will be described in more detail with reference to several examples.

In the first place, the method for preparing H-ZSM-5 catalyst used in some of examples is described.

<CATALYST PREPARATION EXAMPLE>

An aqueous solution was prepared by dissolving aluminum sulfate, sulfuric acid, n-propylamine, and n-propyl bromide into water. Water-glass was added little by little to this solution with stirring to obtain homogeneous gel-like slurry. This slurry was put into an autoclave and crystallized with stirring at 160° C. for 72 hours. After that, the produced crystals were filtered off and water rinsing and filtration were repeated until the filtrate became neutral, thereby obtaining pentasil type zeolite ZSM-5 of 70 in molar ratio ($SiO_2/Al_2O_3$). The thus obtained zeolite was baked in the air and an x-ray diffraction pattern was obtained. This diffraction pattern coincided with the data disclosed in the foregoing Japanese Patent Publication No. 46-10064. Furthermore, by another test, it was-confirmed that the above catalyst had pore-openings of 10-membered oxygen rings.

The above zeolite ZSM-5 were subjected to ion-exchange using hydrochloric acid to obtain a hydrogen type H-ZSM-5 catalyst.

<EXAMPLE 1>

To a 300 ml autoclave with a stirrer (made by Nitto Koatsu K.K.) were added 3 g of commercially available mordenite catalyst, 78 g of benzene, and 8.1 g of chemical reagent grade formaldehyde solution (37 wt. %, made by Kishida Chemical Co., Ltd.) and the contents were stirred at 250° C. for 1 hour. The water content in the reaction system at the start of reaction was 5.2 wt. % and the heating from the room temperature to 250° C. took about 30 minutes. The pressure in the autoclave at 250° C. was 5.5 MPa.

After the reaction, the oily layer was subjected to gas chromatographic (GC) analysis and the degree of conversion of formaldehyde calculated with its result was 27%, and the selectivity of diphenylmethane, 86%.

<EXAMPLE 2>

To a 300 ml autoclave with a stirrer (made by Nitto Koatsu K.K.) were added 3 g of commercially available H-Y type zeolite, 92 g of toluene, and 4.1 g of chemical reagent grade formaldehyde solution (37 wt. %, made by Kishida Chemical Co., Ltd.) and the contents were stirred at 250° C. for 2 hours. The water content in the reaction system at the start of reaction was 2.3 wt. % and the heating from the room temperature to 250° C. took about 34 minutes. The pressure in the autoclave at 250° C. was 2.8 MPa.

After the reaction, the oily layer was subjected to GC analysis and the degree of conversion of formaldehyde calculated with its result was 28%, and the selectivity of ditolylmethane, 92%.,

<EXAMPLE 3>

To a 300 ml autoclave with a stirrer (made by Nitto Koatsu K.K.) were added 3 g of H-ZSM-5 catalyst which was prepared in the above Catalyst Preparation Example, 39 g of benzene, 46 g of toluene, and 4.1 g of chemical reagent grade formaldehyde solution (37 wt. %, made by Kishida Chemical Co., Ltd.) and the contents were stirred at 250° C. for 1 hour. The water content in the reaction system at the start of reaction was 2.5 wt. % and the heating from the room temperature to 250° C. took about 35 minutes. The pressure in the autoclave at 250° C. was 2.6 MPa.

After the reaction, the oily layer was subjected to GC analysis and the degree of conversion of formaldehyde calculated with its result was 50.4%, and the selectivity of diarylalkanes, 97.3%.

<EXAMPLE 4>

To a 300 ml autoclave with a stirrer (made by Nitto Koatsu K.K.) were added 3 g of H-ZSM-5 catalyst prepared in the above Catalyst Preparation Example, 78 g of benzene, and 4.1 g of chemical reagent grade formaldehyde solution (37 wt. %, made by Kishida Chemical Co., Ltd.) and the contents were stirred at 250° C. for 3 hour. The water content in the reaction system at the start of reaction was 2.7 wt. % and the heating from the room temperature to 250° C. took about 30 minutes. The pressure in the autoclave at 250° C. was 3.7 MPa.

After the reaction, the oily layer was subjected to GC analysis and the degree of conversion of formaldehyde calculated with its result was 100%, and the selectivity of diphenylmethane, 80%.

<Comparative Example>

To a 300 ml autoclave with a stirrer (made by Nitto Koatsu K.K.) were added 3 g of a commercially available silica-alumina catalyst (trade name: IS-28, made by Catalyst & Chemical Industries Co., Ltd.), 78 g of benzene, and 4.1 g of chemical reagent grade formaldehyde solution 37 wt. %, made by Kishida Chemical Co., Ltd.) and the contents were stirred at 250° C. for 3 hours. The water content in the reaction system at the start of reaction was 2.7 wt. % and the heating from the room temperature to 250° C. took about 32 minutes. The pressure in the autoclave at 250° C. was 4.1 MPa.

After the reaction, the oily layer was subjected to GC analysis and the degree of conversion of formaldehyde calculated with its result was 3.1%.

It will be understood in view of the above description that diarylalkanes can be synthesized using inexpensive formalin as a starting material according to the method of the present invention.

What is claimed is:

1. A method for producing diarylmethanes comprising reacting a mixture of an aromatic hydrocarbon and formalin, said mixture containing 1.5 to 12% by weight of water, and the reaction being at a temperature in the range of 170° C. to 450° C. under an elevated pressure in the presence of a zeolitic catalyst.

2. The method for producing diarylmethanes as claimed in claim 1, wherein said aromatic hydrocarbon is benzene and/or toluene.

3. The method for producing diarylmethanes as claimed in claim 1, wherein said zeolitic catalyst is a zeolite having pore-openings of 10-membered oxygen rings, or a zeolite having pore-openings of 12-membered oxygen rings, or a mixture thereof.

4. The method for producing diarylmethanes as claimed in claim 1, wherein said reaction is carried out under an elevated pressure which is higher than an autogenous pressure of the reaction system.

5. The method for producing diarylmethanes as claimed in claim 2, wherein said reaction is carried out under an elevated pressure which is higher than an autogenous pressure of the reaction system.

6. The method for producing diarylmethanes as claimed in claim 3, wherein said reaction is carried out under an elevated pressure which is higher than an autogenous pressure of the reaction system.

* * * * *